United States Patent [19]
Scholz et al.

[11] Patent Number: 5,750,136
[45] Date of Patent: May 12, 1998

[54] BIOADHESIVE COMPOSITION AND PATCH

[75] Inventors: Matthew T. Scholz, Woodbury; Robert A. Scherrer, White Bear Lake; Nelda M. Marecki, May; Yen-Lane Chen, New Brighton; Joan K. Barkhaus, Minneapolis, all of Minn.

[73] Assignee: Riker Laboratories, Inc., St. Paul, Minn.

[21] Appl. No.: 456,021

[22] Filed: May 31, 1995

Related U.S. Application Data

[63] Continuation of Ser. No. 842,222, Feb. 26, 1992, abandoned, which is a continuation of Ser. No. 607,863, Nov. 1, 1990, abandoned, which is a continuation-in-part of Ser. No. 486,554, Feb. 27, 1990, abandoned, which is a continuation-in-part of Ser. No. 431,664, Nov. 3, 1989, abandoned.

[51] Int. Cl.[6] .................. A61K 9/10; A61K 15/58; A61K 47/32; C09J 113/00
[52] U.S. Cl. .................. 424/448; 424/434; 424/435
[58] Field of Search ................... 424/434, 448, 424/435

[56] References Cited

U.S. PATENT DOCUMENTS

| | | | |
|---|---|---|---|
| 3,339,546 | 9/1967 | Chen et al. | 128/156 |
| 4,253,460 | 3/1981 | Chen et al. | 128/283 |
| 4,292,299 | 9/1981 | Suzuki et al. | 424/16 |
| 4,393,080 | 7/1983 | Pawelchak et al. | 428/355 |
| 4,470,814 | 9/1984 | Chang et al. | 433/168 |
| 4,551,490 | 11/1985 | Doyle et al. | 524/22 |
| 4,573,996 | 3/1986 | Kwiatek et al. | 604/897 |
| 4,615,697 | 10/1986 | Robinson | 604/890 |
| 4,668,232 | 5/1987 | Cordes et al. | 604/897 |
| 4,740,365 | 4/1988 | Yukimatsu et al. | 424/435 |
| 4,772,470 | 9/1988 | Inoue et al. | 424/435 |
| 4,876,092 | 10/1989 | Mizobuchi et al. | 424/435 |
| 4,983,392 | 1/1991 | Robinson | 424/434 |
| 5,047,244 | 9/1991 | Sanuordeker et al. | 424/434 |
| 5,225,196 | 7/1993 | Robinson | 424/434 |

FOREIGN PATENT DOCUMENTS

| | | | |
|---|---|---|---|
| 390541 | 10/1990 | European Pat. Off. | |
| 399518 | 10/1990 | European Pat. Off. | |
| 56-068608 | 6/1981 | Japan | |
| 61-30517 | 2/1986 | Japan | 424/434 |

Primary Examiner—Peter F. Kulkosky
Attorney, Agent, or Firm—MarySusan Howard; Ted K. Ringsred; Walter N. Kirn

[57] ABSTRACT

A bioadhesive composition that adheres suitably to a mucosal surface and is capable of delivering drugs in sustained fashion, and a patch comprising the bioadhesive composition. Methods of using and processes for preparing the bioadhesive composition are also described.

52 Claims, No Drawings

5,750,136

BIOADHESIVE COMPOSITION AND PATCH

CROSS REFERENCE TO RELATED APPLICATION

This application is a continuation of U.S. Ser. No. 07/842,222, filed Feb. 26, 1992, now abandoned; which is a continuation of U.S. Ser. No. 07/607,863, filed Nov. 1, 1990, now abandoned; which is a continuation-in-part of U.S. Ser. No. 07/486,554, filed Feb. 27, 1990, now abandoned; which is a continuation-in-part of U.S. Ser. No. 07/431,664, filed Nov. 3, 1989, now abandoned.

BACKGROUND OF THE INVENTION

1. Field of the Invention

This invention relates to mucosal adhesives. In another aspect this invention relates to compositions that adhere to oral mucosa. In yet another aspect this invention relates to methods of transmucosal drug delivery.

2. Description of the Related Art

Buccal tablets and like devices are known and disclosed for example in U.S. Pat. Nos. 4,740,365 and 4,764,378. These devices adhere to mucosal surfaces and dissolve or otherwise disintegrate over time, thus delivering drug into the mouth of the patient in a sustained fashion. It is also known that delivery of drugs across the oral mucosa avoids hepatic first-pass inactivation, inactivation by gastrointestinal fluids, and other modes of inactivation characteristic of oral drug ingestion. Sustained release adhesive bandages, patches, and the like that contain drugs and adhere to mucosal surfaces are known to the art. Polyacrylic acids and polyisobutylenes have been disclosed as components of such adhesives. For example, U.S. Pat. No. 3,339,546 (Chen) discloses a bandage that is said to adhere to moist surfaces of the oral cavity and comprises a medicament and a hydrocolloid incorporated in a natural or synthetic gum-like substance. Carboxypolymethylene (i.e., polyacrylic acid) is among the hydrocolloids disclosed, and polyisobutylene is among the gum-like substances disclosed.

U.S. Pat. No. 4,615,697 (Robinson) discloses a composition including a bioadhesive and a treating agent. The bioadhesive is a water-swellable but water insoluble, fibrous, crosslinked, carboxy-functional polymer containing (a) a plurality of repeating units of which at least about 80% contain at least 1 carboxy functionality, and (b) about 0.05 to about 1.5% of a cross-linking agent substantially free from polyalkenyl polyether. The specifically excluded type of crosslinker is said to be the type used in CARBOPOL™ 934 resin (commercially available from B. F. Goodrich, Specialty Chemicals and Polymers Division, Cleveland, Ohio). CARBOPOL™ 934 resin is said to be water soluble and therefore undesirable as a bioadhesive in the Robinson composition.

U.S. Pat. No. 4,253,460 (Chen et al.) discloses an adhesive composition consisting of a mixture of a hydrocolloid gum, a pressure sensitive adhesive, and a cohesive strengthening agent. The pressure sensitive adhesive component can be a mixture of three to five parts of a polyisobutylene with a viscosity average molecular weight of about 36,000 to about 53,000 and one part of an elastomer such as a polyisobutylene with a viscosity average molecular weight of about 1,150,000 to about 1,600,000.

U.S. Pat. No. 4,740,365 (Yukimatsu et al.) discloses a sustained-release preparation comprising an active ingredient and a mixture of two polymer components, the first of which comprises one or more polymers selected from poly- acrylic acid and a pharmaceutically acceptable salt thereof, and the second being selected from the group consisting of polyvinylpyrrolidone, polyvinyl alcohol, polyethylene glycol, alginic acid, and a pharmaceutically acceptable salt of alginic acid. CARBOPOL™ resins are among the polymers said to be suitable members of the first-mentioned class of polymers.

U.S. Pat. No. 4,772,470 (Inoue, et al.) discloses an oral bandage comprising a mixture of a polyacrylic acid and a vinyl acetate polymer in a compatible state. This bandage is said to exhibit strong adhesion of long duration when applied to oral mucosa or teeth.

SUMMARY OF THE INVENTION

This invention provides a bioadhesive is composition that comprises:

1) a particulate polymeric resin with an average particle size of less than or equal to about 100 μm and comprising at least about 55% by weight of carboxylic acid moieties based on the total weight of the polymeric resin;

2) from about 20 parts to about 250 parts by weight of a hydrophobic elastomeric component, based on 100 parts by weight of the resin; and 3) an amount of a drug effective to provide a desired therapeutic result, wherein the resin and the drug are dispersed substantially throughout the elastomeric component, and which composition contains less than about 10% water by weight based on the weight of the polymeric resin, exhibits substantially no instantaneous adhesion to dry skin, and adheres to a mucosal surface.

A bioadhesive composition of this invention exhibits good adherence to human oral mucosa. In particular embodiments, this invention provides a bioadhesive composition as described above that exhibits a duration of adhesion to human oral mucosa of at least about 6 hours when tested according to the Test Method described in detail below. Also, the drug is released in sustained fashion over a prolonged period to a mucosal surface for, for example, local or systemic treatment.

In a preferred embodiment when systemic treatment is desired, the bioadhesive composition has a backing such as a flexible film applied to it.

Further, in yet another preferred embodiment the resin is covalently crosslinked with about 0.75% to about 2% by weight, based on the total weight of the resin, of a polyalkenyl polyether. The preferred resin can also be partially neutralized (e.g., up to about 30%) with a base of mono, di- or trivalent metal, or with a polyamine.

This invention also provides therapeutic methods. One such method is a method of achieving and/or maintaining a therapeutically effective blood level of a drug in a mammal, comprising the steps of:

a) adhering a composition of the invention to a mucosal surface of a mammal; and b) allowing the composition to remain adhered for a time sufficient to release the drug such that a therapeutically effective blood level of drug is achieved and/or maintained.

Another such method is a method of delivering a drug to a mucosal surface of a mammal or to the vicinity of a mucosal surface of a mammal to provide a therapeutic effect on or in the vicinity of the mucosal surface, which method comprises the steps of:

a) adhering a composition of the invention to the mucosal surface;

b) allowing the composition to remain adhered for a time sufficient to release the drug to the mucosal surface or to the vicinity of the mucosal surface to provide the desired therapeutic effect.

A composition of the invention can be used to administer drugs systemically (e.g., across the oral or aginal mucosa or other mucosal surfaces) or locally (e.g., to the oral or vaginal cavity). A composition of the invention exhibits sustained delivery of basic, acidic, and neutral drugs, and salts thereof and allows the delivery rate to be tailored as desired. In the case of delivery of a drug across the oral mucosa, a composition of the invention can also minimize the loss of a drug to the gastro-intestinal tract. A composition of the invention is also soft and conformable such that it can be worn comfortably by the user.

DETAILED DESCRIPTION OF THE INVENTION

The polymeric resin component of a composition of the invention comprises at least about 55% by weight of carboxylic acid moieties based on the total weight of the resin. Suitable carboxylic acid-containing monomers include acrylic acid, maleic acid, itaconic acid, citraconic acid, methacrylic acid, and the like, and combinations thereof. Acrylic acid is preferred. The polymeric resin can also comprise minor amounts (e.g., less than about 20 percent by weight based on the total weight of all monomers in the polymer) of comonomers that are polymerizable with the carboxylic acid-containing monomer, such as methyl vinyl ether, lower alkyl (meth) acrylates, and the like.

Linear polyacrylic acid resins with a molecular weight between about 400,000 and about 5,000,000 have been found to be suitable for use in a composition of the invention. More preferred, however, are crosslinked resins. Most preferred resins include those comprising polyacrylic acid with a molecular weight between about 750,000 and about 4,000,000, preferably about 2,000,000 to about 4,000,000, and more preferably about 3,000,000, crosslinked with about 0.75% to about 2% by weight, based on the total weight of the resin, of a polyalkenyl polyether such as an allyl ether of sucrose or an allyl ether of pentaerythritol. Particularly preferred resins of this type include the resins available under the trade designation CARBOPOL™ resin (e.g., CARBOPOL™ resins 910, 934, 934P, 941, 951, and 1342 from B. F. Goodrich Co., Specialty Polymers and Chemical Division, Cleveland, Ohio). CARBOPOL™ 934P resin is most preferred, as it is generally recognized as acceptable for pharmaceutical applications. Another suitable resin is "polycarbophil", a material commercially available from A. H. Robins Co., Richmond, Va., and described in USP XX as a polyacrylic acid crosslinked with divinylglycol.

A polyacrylic acid resin or a crosslinked resin such as those enumerated above can be partially neutralized by a base of an alkali metal, or by a base of a divalent or trivalent metal (e.g., $Zn^{+2}$, $Ca^{+2}$, $Mg^{+2}$, or $Al^{+3}$). Basic polyamines such as Eudragit™ E (a copolymer of dimethylaminoethyl methacrylate and neutral methacrylates, available from Rohm Pharma, Weiterstadt, Germany) are also suitable for use in neutralizing a resin. In such a resin, up to about 30% of the carboxylic acid moieties in the resin can be neutralized by a base. Preferred bases include $Al(OH)_3$ and $Ca(OH)_2$.

The particle size of the resin affects the adhesion of a composition of the invention to mucosal surfaces, the rate of disintegration, and the rate at which a composition releases drug. Proper particle size affords a composition with sufficient surface area of the resin available to provide good adhesion, but not so much that the composition rapidly disintegrates when placed on a mucosal surface, e.g., in the oral cavity. Average particle size can be up to about 100 µm. It is preferred that the resin have an average particle size of between about 1 µm and about 80 µm, more preferably between about 1 µm and about 30 µm, and most preferably between about 2 µm and about 10 µm.

It is desirable to keep the level of moisture low in a bioadhesive composition of the invention. A bioadhesive composition has a water content of less than about 10% by weight, preferably less than about 6%, more preferably less than about 4% by weight, and most preferably less than about 2% by weight based on the total weight of the resin. In order for the composition to have the requisite low water content the resin, prior to incorporation in the composition, is preferably dried to the desired level and protected from ambient moisture. Once the resin is incorporated in a composition of the invention, ambient moisture is no longer generally of concern, as the resin, which is generally hygroscopic, is protected from ambient moisture by the hydrophobic elastomeric component. A composition can be stored for at least several months at ambient humidity without adversely affecting its adhesive properties.

By itself, a polymeric resin as described above generally possesses insufficient structural integrity. Such acidic resins can also be irritating to mucosal tissue. Further, a resin alone provides no means of controlled hydration and sustained release of drug. To remedy these deficiencies, the resin is substantially dispersed throughout a hydrophobic elastomeric component.

The relative amounts of the polymeric resin and the hydrophobic elastomeric component can affect both the duration of adhesion and the drug release properties of a composition of the invention. Generally a composition of the invention comprises about 20 parts to about 250 parts, preferably about 20 parts to about 150 parts, and most preferably 25 to about 75 parts by weight of a hydrophobic elastomeric component, based on 100 parts by weight of the resin.

Suitable elastomeric components preferably are soft such that the ultimate composition can be worn without significant discomfort to the user. Further, they are such that a composition of the invention does not exhibit excessive cold-flow when stored at room temperature. The hydrophobic elastomeric component preferably has a surface energy of less than about 40 dyne/cm and more preferably has a surface energy of less than about 30 dyne/cm.

Examples of materials suitable for use in an elastomeric component include: hydrocarbons such as block styrene-butadiene-styrene copolymers and block styrene-isoprene-styrene copolymers, such as those available from Shell Chemical Co. as Kraton™ rubbers, polyolefins such as polyisobutylenes, polybutadienes, butyl rubber (a copolymer of isobutylene and isoprene), and isoprene rubbers, e.g., polyisoprene (such as that available as LIR-50 polyisoprene from Arakawa Chemical Co., Chicago, Ill. and NATSYN™ polyisoprene from Goodyear, Akron, Ohio); functionalized polyolefins such as functional polyisoprenes, e.g., carboxy-functional polyisoprenes (such as that available as LIR-410 functional polyisoprene, also from Arakawa) and hydroxy-functional polyiso-prenes (such as that available as LIR-506 polyisoprene, Arakawa); and mixtures and blends of two or more of the foregoing.

Another class of material suitable for use in an elastomeric component includes acrylate elastomers. Suitable acrylate elastomers include polymers and copolymers comprising at least about 60 percent by weight based on the total weight of all monomers in the polymer of a hydrophobic monomeric acrylic or methacrylic acid ester of an alkyl alcohol, the alkyl alcohol containing 4 to 10 carbon atoms. Some such elastomers are disclosed in U.S. Pat. No. 4,751,087 (Wick) the disclosure of which is incorporated herein by reference. Particularly suitable are those acrylate copolymers containing A and B Monomers as follows: Monomer A is a hydrophobic monomeric acrylic or methacrylic acid ester of an alkyl alcohol, the alkyl alcohol containing 4 to 10 carbon atoms, preferably 8 carbon atoms. Examples of suitable A Monomers are n-butyl, n-pentyl, n-hexyl, isoheptyl, n-nonyl, n-decyl, isohexyl, isooctyl, 2-ethyloctyl, and 2-ethylhexyl acrylates. The most preferred A Monomer is isooctyl acrylate. Monomer B is a reinforcing monomer selected from the group consisting of acrylic acid; methacrylic acid; alkyl acrylates and methacrylates containing 1 to 3 carbon atoms in the alkyl group; acrylamide; methacrylamide; and lower alkyl-substituted acrylamides (i.e., the alkyl group containing 1 to 4 carbon atoms) such as tertiary-butyl acrylamide. The most preferred B Monomer is acrylamide. In such an elastomer, the A Monomer is preferably present in an amount by weight of about 80 percent to about 98 percent, and the B Monomer is preferably present in an amount by weight of about 2 to about 20 percent of the total weight of the monomers in the copolymer. While such acrylate copolymers per se are pressure-sensitive adhesives, when they are incorporated into a composition of the invention, the composition exhibits substantially no instantaneous adhesion to dry skin.

Hydrocarbons are the most preferred materials for use in an elastomeric component. Preferred hydrocarbon elastomeric components, particularly when the composition is prepared by the solvent casting method set forth in detail below, include polyisobutylene mixtures comprising, based on the total weight of the polyisobutylene mixture, from about 5% to about 50% preferably abut 15% to about 25%, and most preferably about 20% weight of a polyisobutylene with a viscosity average molecular weight between about 500,000 and about 2,500,000, preferably about 1,250,000, and from about 50% to about 95%, preferably about 75% to about 85%, and most preferably about 80%, by weight of a polyisobutylene with a viscosity average molecular weight between about 40,000 and about 100,000, preferably about 53,000. Particularly preferred is an elastomeric component made by the solvent-casting method and consisting of about 80% by weight of VISTANEX™ LM-MH polyisobutylene and about 20% by weight of VISTANEX™ L-100 polyisobutylene.

In contrast to solvent-casting processes, the milling process (set forth in detail below) can reduce substantially the average molecular weight of the polymers that are used in the process. For example, some preferred polyisobutylene elastomers in embodiments made by the milling process are made from the preferred polymers enumerated above but they have molecular weights somewhat lower than the molecular weight ranges set forth above. Another preferred elastomeric component when the composition is prepared by the milling method is a polyisobutylene mixture made from about 60 to about 100% by weight a polyisobutylene with a viscosity average molecular weight of about 750,000 to about 1,500,000 most preferably about 900,000, and 0% to about 40% of a polyisobutylene with a viscosity average molecular weight of about 40,000 to about 100,000, most preferably about 53,000.

Further preferred elastomeric components, particulary for use when the milling method is employed, comprise polyisoprene, polybutadiene, or a mixture thereof. Polyisoprenes having molecular weights of about 500,000 to about 1,200,000, and mixtures thereof, are suitable. Polybutadienes having a molecular weight of about 100,000 to about 500,000, and mixtures thereof, are suitable. Mixtures of such polyisoprenes and polybutadienes are also suitable. A particularly preferred elastomeric component when the composition is prepared by the milling method is made from a mixture of about 20 to about 80 percent by weight, preferably about 50 percent by weight, of a polybutadiene having a molecular weight of about 375,000 and about 20 to about 80 percent by weight, preferably about 50 percent by weight, of a polyisoprene having a molecular weight of about 760,000.

Exemplary specific polyisobutylenes suitable for use in the above-described elastomeric components include those commercially available from Exxon Chemical Co., Houston Tex., under the trade designation VISTANEX™ polyisobutylene and those commercially available from BASF under the trade designation OPPANOL™ polyisobutylene. Preferred polyisobutylenes include VISTANEX™ LM-MH polyisobutylene (viscosity average molecular weight about 53,000), VISTANEX™ L-80 polyisobutylene (viscosity average molecular weight about 900,000), and VISTANEX™ L-100 polyisobutylene (viscosity average molecular weight about 1,250,000). Exemplary specific polyisoprenes suitable for use include those commercially available from Goodyear, Akron, Ohio, under the designation NATSYN™ polyisoprene. Preferred polyisoprenes include NATSYN™ 2210 polyisoprene (weight average molecular weight about 760,000) and NATSYN™ 2205 polyisoprene (weight average molecular weight about 955,000). Exemplary specific polybutadienes suitable for use include those commercially available from Polysar, Akron, Ohio under the trade designation TAKTENE™ polybutadiene. Preferred polybutadienes include TAKTENE™ 1202 polybutadiene (weight average molecular weight about 375,000).

For purposes of the instant specification and claims, the term viscosity average molecular weight means Flory molecular weight as determined by the method set forth in "Food Chemicals Codex", 3rd Ed. page 469, 1981, National Academy Press, incorporated herein by references.

An elastomeric component can also comprise a plasticizer such as mineral oil, silicone oil, corn oil, and the like. A particularly preferred elastomeric component of this type is a mixture comprising mineral oil and linear styrene-isoprene-styrene block copolymer such as that commercially available from Shell Chemical, Houston, Tex., under the trade designation KRATON™ D 1107 rubber. It is preferred that an elastomeric component of this type comprise from about 20 percent to about 40 percent, more preferably about 33 percent, by weight of mineral oil and correspondingly from about 60 percent to about 80 percent, more preferably about 67 percent, by weight of the block copolymer.

The resin can be substantially uniformly dispersed throughout the elastomeric component, or it can be present in any suitable gradient, e.g., a gradient wherein there is a substantially higher concentration of the resin nearer the surface that is intended to be adhered to a mucosal surface. The term "gradient" as used herein represents a continuous or discontinuous variation in concentration across the cross-sectional thickness of a composition.

A bioadhesive composition of the invention also comprises a drug. Drugs that can be delivered include those useful for the local treatment of the mouth or throat, or the vaginal cavity, in addition to those useful for systemic treatment via delivery through mucosal tissue. They include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such is as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals. (e.g., nystatin); coronary vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone, testosterone, estradiol); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinoline-4-amine, and other compounds disclosed in U.S. Pat. No. 4,689,338, incorporated herein by reference, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones, LHRH); cardioactive products such as atriopeptides; proteinaceous products (e.g., insulin); enzymes (e.g., anti-plaque enzymes, lysozyme, dextranase); antinauseants (e.g., scopoloinine); anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatripan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; and the like, as well as pharmaceutically acceptable salts and esters thereof. Preferred drugs include digoxin, heparin, hydromorphone, morphine, melatonin, buprenorphine, and pharmaceutically acceptable salts thereof.

A drug is preferably incorporated neat into a composition of the invention. The drug is preferably present in an effective amount, which will depend upon the particular drug used, the intended therapy, and the desired duration of use of a particular individual application of the composition containing the drug. Practical limitations on the amount of drug incorporated in a composition are that amount above which the composition begins to lose adhesion to a mucosal surface, and that amount below which a therapeutically effective blood level of drug cannot be achieved and/or maintained. Generally, the preferred range is from about 0.1% to about 25% by weight based on the total weight of the bioadhesive composition. Preferably, the drug will be capable of release from the composition in a sustained fashion over a prolonged period (i.e., at least about 6 hours and preferably at least about 12 hours).

The drug is generally dispersed throughout the elastomeric component. The drug can be substantially uniformly dispersed, or it can be distributed in any suitable gradient, e.g., a gradient wherein drug concentration is greater nearer the surface that is intended to be adhered to a mucosal surface, or a gradient wherein drug concentration is lower nearer the surface that is intended to be adhered to a mucosal surface, in order to achieve the desired blood-level profile.

A composition can contain other ingredients, for example excipients such as flavorings or flavor-masking agents, dyes, penetration enhancers, water-soluble or water-swellable fibrous reinforcers, and the like under circumstances and in amounts easily determined by those skilled in the art. Penetration enhancers have particular utility when used with drugs such as peptides and proteins. Suitable penetration enhancers include anionic surfactants (e.g., sodium lauryl sulfate); cationic surfactants (e.g., cetylpyridinium chloride); nonionic surfactants (e.g., polysorbate 80, polyoxyethylene 9-lauryl ether, glyceryl monolaurate); lipids (e.g., oleic acid); bile salts (e.g., sodium glycocholate, sodium taurocholate); and related compounds (e.g., sodium tauro-24,25-dihydrofusidate). Like the drug discussed above, such ingredients can be dispersed substantially uniformly in the composition or dispersed in any suitable gradient therein.

A resin useful in a composition of this invention can be prepared using conventional procedures and conventional laboratory equipment. For example, such resins can be prepared from acrylic acid and the appropriate crosslinkers by methods well known to those killed in the art, and disclosed for example in U.S. Pat.

No. 2,798,053 (Brown). A commercially available polyacrylic acid resin or a commercially available particulate resin such as the CARBOPOL™ resins discussed above can be used as received if it is available in an appropriate particle size and with a suitably low water content.

Conventional drying methods, preferably using temperatures less than about 95° C., and more preferably less than about 50° C., can be used to dry a resin to the desired degree, e.g., less than about 2% water content. Further, if it is desired to increase or decrease the particle size, a resin can be wet-granulated by first wetting and stirring with a polar solvent (e.g., isopropyl alcohol), drying to the desired degree (e.g., in a tray oven), and then milling to a powder of the desired size. Particle size can also be adjusted by other conventional techniques, with the caveat that substantial degradation of the resin is to be avoided.

To prepare a neutralized resin as discussed above, a particulate polyacrylic acid resin or a particulate covalently crosslinked resin can be suspended by vigorously stirring in a water-soluble solvent (e.g., ethanol, isopropyl alcohol, or methanol). To this suspension, an aqueous solution containing the polyamine or the desired base of a metal can be added. Upon vigorous agitation (e.g., shaking overnight in a conventional laboratory shaker) a homogeneous mixture containing the neutralized resin obtains. Drying this mixture, for example by spray drying, affords a free-flowing powder. With high concentrations of base, a spray drying process can become more time consuming than desired, in which case a wet-granulation process might be preferred. In such a process, the polyacrylic acid resin and the base can first be mixed as solids, then moistened with a polar solvent (e.g., isopropyl alcohol) and stirred. Under such conditions, it is possible that significant neutralization does not occur. However, when the resulting resin is incorporated into a composition of the invention as described below, and the composition is placed on a moist surface such as a mucosal surface, it is possible that further neutralization occurs in situ. For the purposes of the instant specification and claims, a material so made is termed a neutralized resin prior to presumed further in situ neutralization. In any case, the resulting mixture can then be dried to the desired degree and milled using conventional apparatus to form a powder of the desired particle size.

A suitable resin can then be formulated into a composition of the invention by a solvent-casting method that involves dispersing the resin, e.g., with stirring, in a solution of an elastomeric component in a volatile organic solvent, such as hexane or toluene, to form a resin/elastomeric component/ solvent mixture. A drug and any excipient or other ingredient can be incorporated by first adding it and then the resin, or vice-versa, to a solution of the elastomeric component in a volatile organic solvent. Alternatively, a drug and any excipient or other ingredient can be incorporated by first adsorbing it on the resin or on an inert support such as silica, absorbing it into the resin, or ionically binding it to the resin. The composition can then be made into a sheet. This can be done by coating (e.g., using a knife coater) a suitable release liner with a uniform thickness of a resin/elastomeric component/solvent mixture containing the drug and any excipient or other ingredient and allowing the solvent to be removed without substantial foaming or bubbling caused by solvent release, e.g., by evaporation in air or by drying methods well known to those skilled in the art.

As an alternative that avoids the use of added solvents, the components of a composition can be milled together neat using mill such as a conventional rubber mill (e.g., a two-roll mill). If the elastomeric component comprises more than one ingredient, these ingredients can be milled together first to form a substantially homogeneous elastomeric component. The polymeric resin and the drug and any excipient or other ingredients can then be milled with the substantially homogeneous elastomeric component in order to form a substantially homogeneous composition of the invention. In some cases it is necessary to heat or cool the rolls in order to assure good mixing and in order to facilitate removal of the composition from the rolls. The drug and any excipient or other ingredients can be added neat to the polymeric resin prior to milling. Alternatively, they can be adsorbed on the resin, adsorbed on an inert support such as silica, absorbed into the resin, or ionically bound to the resin by conventional methods prior to milling. The composition can then be made into a sheet by, for example, pressing between two sheets of release liner in a heated platen press at a pressure of about 35,000 to about 175,000 KPa and at a temperature of about 50° C. The milling method is particularly amenable to the preparation of compositions wherein the resin and/or the drug is distributed throughout the composition in a suitable gradient as described above.

The preferred thickness of the final dry sheet of composition (irrespective of the method of preparation) is from about 0.5 mm to about 5 mm, more preferably from about 1 mm to about 3 mm. Gradient distribution can be carried out by preparing two or more sheets of differing composition and optionally differing thickness (e.g., in the range from about 0.20 mm to about 1 mm) and laminating them together, e.g., between two sheets of release liner in a heated platen press to produce a composition with the desired gradient. Shims can be used to control the final thickness.

If desired, additional polymeric resin can be spread substantially uniformly on one surface of a sheet of a composition. The composition can then be pressed between two sheets of release liner in order to embed the additional polymeric resin into the composition.

Suitable release liners for use in the above-described methods of preparation include conventional release liners comprising a known sheet material, such as a polyester web, a polyethylene web, or a polystyrene web, or polyethylene-coated paper, coated with a suitable silicone-type coating such as Daubert 164-Z (commercially available from Daubert Co., Elmhurst, Ill.).

If desired, a backing material can then be applied to the composition using methods well known to those skilled in the art. The backing material is preferably a flexible film that prevents bulk fluid flow and is inert to the ingredients of the composition. In the case of a composition that contains a drug intended to be delivered across a membrane such as a mucosal surface and intended to have systemic action, the backing is preferably substantially resistant to the migration of the drug therethrough. In the case of a composition that contains a drug intended to be delivered, e.g., to the oral cavity or the vaginal cavity and/or intended to have local action, the backing can be permeable to the agent to be delivered and can be permeable to saliva as well. The backing material can be any of the conventional materials used as backing for tapes or dressings, such as polyethylene, polypropylene, ethylene-vinyl acetate copolymer, ethylene propylene diene copolymer, polyurethane, rayon, and the like. Non-woven materials such as polyesters, polyolefins, and polyamides can also be used. Also, a layer of a hydrophobic elastomer such as polyisobutylene can function as a backing. Preferred backing materials include an acrylate pressure-sensitive adhesive coated polyurethane film such as TEGADERM™ brand surgical dressing (commercially available from the 3M Company, St. Paul, Minn.).

A composition with a backing applied thereto can be made into a patch with a backing by die-cutting individual patches from the sheet. Alternatively, a patch with no backing can be prepared by die-cutting individual patches from a coated release liner prepared by the solvent method set forth above or by die-cutting from a sheet of bioadhesive composition prepared by pressing between, two sheets of release liner. A patch can be of any suitable size and shape, e.g., a 1 cm$^2$ circular disk.

Particular embodiments of the invention use no backing or a backing that is substantially permeable to the bodily fluid with which the composition is in contact (e.g., saliva). In such embodiments, it is preferred that the composition exhibit substantially no disintegration over the time period during which the composition is intended to remain adhered to the mucosal surface. This provides for sustained release of the drug over a prolonged period of time.

Other particular embodiments of the invention use a backing that is substantially impermeable to the bodily fluid with which the composition is in contact. In such embodiments, the backing further protects the composition from substantial disintegration over the time period during which the composition is intended to remain adhered to the mucosal surface. However, even in such embodiments a lack of substantial disintegration of the bioadhesive composition itself can serve to optimize the delivery of a drug to the mucosal surface (as opposed to delivery of the drug to the vicinity of the mucosal surface, e.g., to the oral cavity).

"Substantially no disintegration" as used herein means that a bioadhesive composition is resistant to disintegration such that, when the composition having no backing attached thereto is adhered in the oral cavity and tested as set forth in the Test Method below, the composition covers at least about 50% of the area after it is adhered for a designated period of time as is covered by the composition initially.

While compositions of the invention adhere to mucosal surfaces, they exhibit substantially no instantaneous adhesion to dry skin. A composition or a patch of the invention can therefore be handled by a patient without undue concern that the composition or patch will have its mucosal adhesive properties compromised by adhering to the skin or to another dry surface, prior to placement on the mucosa.

A composition of the invention or a patch made from a composition of the invention can be applied to a mucosal surface, such as the oral mucosa, e.g., the buccal mucosa or gingival mucosa, of a mammal and replaced as desired (e.g., as is necessary or as is convenient to the user) with a fresh patch, e.g., to maintain a therapeutically effective blood level of a drug. The opposing surfaces of a composition or a patch with no backing can be adhered to opposing mucosal surfaces, e.g., the gum and the cheek or lip, thereby providing added adhesion and a means of simultaneous drug delivery to two mucosal surfaces from the same patch. A composition or a patch of the invention exhibits sustained release of a drug such that a therapeutically effective blood level of the drug can be achieved and/or maintained in a mammal for an extended period of time. Also, a therapeutic level of drug can be maintained in the vicinity of the mucosal surface (e.g., in the oral cavity or the vaginal cavity) if the treatment being effected is local rather than systemic.

In particular embodiments of the invention, a bioadhesive composition or a patch will adhere to human oral mucosa for at least 6 hours, more preferably for at least 8 hours, and most preferably at least 12 hours when tested as described below.

Test Method

For purposes of determining the duration of adhesion of a bioadhesive composition of the invention to human oral mucosa, the following method (hereinafter referred to as the "Test Method") is employed as follows.

Step 1. A bioadhesive composition is made into individual patches as follows: An appropriate amount of a substantially solvent-free sample of the bioadhesive composition is placed in a two-roll mill and milled at room temperature until a substantially uniform composition obtains. The composition is then pressed between 2 sheets of silicone-coated release liner in a double heated platen press at a pressure of 70,000 KPa and a temperature of 50° C. to afford the composition in the form of a 1 mm thick sheet. One sheet of the release liner is removed, and the exposed bioadhesive surface is contacted with the adhesive surface of a 20 µm thick polyurethane backing material that has an acrylate pressure-sensitive adhesive coated thereon, to provide a bioadhesive-coated sheet material. Individual patches are then die cut using a 1 cm² circular die.

Step 2. A total of six healthy subjects (3 male, 3 female) between the ages of 25 and 55 years who have been otherwise selected randomly are studied. The subjects fast for at least 1 h prior to the placement of the patch. The release liner (if any) of a patch is removed and the patch is pressed into place with a minimal force (i.e., a force sufficient to allow the patch to adhere but not so great as to cause discomfort) on the oral mucosa of a subject [i.e., at the location prescribed by the instructions (e.g., a package insert) accompanying the particular patch being tested, or absent such instructions, on the upper gingival mucosa above a canine tooth] and held there for several seconds, care being taken to assure that the exposed bioadhesive surface of the patch is not contacted with moist skin, water, mucous, or a mucosal surface prior to placement. The data in the examples below involve placement on the upper gingival mucosa above a canine tooth. If the patch does not adhere to a particular subject, an attempt is made to adhere a second patch. If the second patch does not adhere, that subject is dismissed from the study and replaced with another subject selected as set forth above. Once the patch is in place, the subjects engage in the normal activities of daily living, taking care to not forcibly dislodge the patch, e.g., with their tongue, a toothbrush, or while chewing food. If the patch is forcibly dislodged during the study, a new patch is placed as described above and the study with respect to that subject is begun anew. The elapsed time in hours before the patch loses adhesion as noted by the subject is measured and recorded. The average elapsed time in hours observed for the six subjects is then determined. Should it be desired to measure disintegration over a designated period of time by the Test Method, the backing (if any) of the patch is removed prior to placement of the patch, the area covered by the patch after adhesion for the designated period is noted, and the average area that remains covered in the six subjects is determined.

In one embodiment of the invention, a bioadhesive composition exhibits a duration of adhesion of at least about 6 hours when tested according to this Test Method.

For purposes of determining the duration of adhesion of a patch of the invention to human oral mucosa, whether the patch has been prepared according to Step 1 of the Test Method or otherwise, Step 2 of the Test Method is employed.

In one embodiment of the invention, a patch of the invention exhibits a duration of adhesion of at least about 6 hours when tested according to Step 2 of the Test Method.

The procedures described below set forth non-limiting methods of preparing partially neutralized resins suitable for use in a bioadhesive composition of the invention. Other methods can also be employed if a partially neutralized resin is desired.

REPARATIVE METHOD 1

CARBOPOL™ 934 P resin (200 g) and calcium hydroxide (15 g, particle size about 25 µm) were placed in a 5 quart Hobart mixer (Model N-50, Hobart Corp., Troy, Ohio) and mixed for 5 minutes at a setting of 1. Stirring was continued and isopropyl alcohol (about 200 mL) was added dropwise to the mixture over a period of about 5 minutes, resulting in a material of a dough-like consistency. This material was dried overnight in a tray oven at 90° C., and milled in a small mill (Fitzpatrick Model J, Fitzpatrick Co., Elmhurst, Ill.) to afford a resin in the form of a powder with a particle size of about 30–50 µm.

REPARATIVE METHOD 2

CARBOPOL™ 934 P resin (10 g) was added slowly to ethyl alcohol (500 mL). The resulting mixture was stirred vigorously with a magnetic stirrer until the resin was homogeneously suspended. An aqueous solution of calcium hydroxide (780 mL of a solution containing 1 g/L, 780 mg) was added and the mixture was placed in a screw top jar. The jar was placed in an Eberbach laboratory shaker and shaken overnight at room temperature. The resulting mixture was spray dried using a Buchi Model 190 Mini-Spray Drier (Buchi Laboratories, Flawil, Switzerland). A free-flowing powder (5 g) resulted.

PREPARATIVE METHOD 3

CARBOPOL™ 934 P resin (10 g) was added slowly to ethyl alcohol (500 mL). The resulting mixture was stirred vigorously until the resin was homogeneously suspended. An aqueous solution of aluminum hydroxide (0.91 g in 600 mL water) was added, and the mixture was stirred and dried as set forth in Preparative Method 2.

PREPARATIVE METHOD 4

CARBOPOL™ 934 P resin (300 g) and calcium hydroxide (38 g. particle size about 25 μm) were placed in a 5 quart Hobart mixer and mixed for about 5 minutes at a is setting of 1. Stirring was continued and isopropyl alcohol (about 300 mL) was added uniformly over a period of about 5 minutes. The resulting material was dried and milled according to Preparative Method 1 to afford a resin in the form of a powder with a particle size of about 30–50 μm.

The following examples are provided to illustrate the invention. They are not intended to limit the invention. All parts and percentages are by weight unless otherwise indicated. When placebo patches were used to determine adhesion to human buccal mucosa, the duration of adhesion represents the length of time that a patch adhered in one person, unless it is indicated that the Test Method was used.

EXAMPLE 1

A solution containing a polyisobutylene with a viscosity average molecular weight of about 53,000 (1.6 g, as 3.2 g of a stock solution containing 50% by weight VISTANEX™ LM-MH polyisobutylene, commercially available from Exxon Chemical Co., Houston, Tex., in a 1:1 mixture by volume of hexane and toluene) and a polyisobutylene with a viscosity average molecular weight of about 1,200,000 (0.080 g, as 0.4 g of a stock solution containing 20% by weight of VISTANEX™ L-100 polyisobutylene, also commercially available from Exxon Chemical Co., in a 1:1 mixture by volume of hexane and toluene) was prepared. Resin obtained from Preparative Method 2 (3.0 g) was added with stirring. A 1:1 solution of hexane and toluene (5 mL) was added and stirring continued for about 5 minutes. The mixture was then coated using a knife coater onto silicone-coated release liner at a wet thickness of 3.4 mm. The solvent was allowed to evaporate. A backing material, TEGADERM™ 1625 brand surgical dressing, was applied by hand to the exposed surface of the coating to provide a composition with a backing material applied thereto. Individual patches were hand-cut from this sheet material with a 1 cm² circular die.

EXAMPLES 2–4

To prepare the bioadhesive composition of EXAMPLE 2, a solution containing VISTANEX™ L-100 polyisobutylene (0.35 g as 1.75 g of a stock solution containing 20% VISTANEX™ L-100 polyisobutylene by weight in a 1:1 mixture by volume of hexane and toluene) and VISTANEX™ LM-MH polyisobutylene (1.60 g as 3.2 g of a stock solution containing 50% VISTANEX™ LM-MH polyisobutylene by weight in a 1:1 mixture by volume of hexane and toluene) was prepared. Digoxin (0.05 g) was added with stirring. Resin obtained from Preparative Method 2 (3.0 g) was added with stirring. A 1:1 mixture by volume of toluene and hexane (5 mL) was added, and stirring was continued for about 5 minutes. The resulting mixture was made into patches according to the method of EXAMPLE 1.

Similarly, using the same relative amounts of components, resin obtained from Preparative Method 3 was combined with digoxin and incorporated into a patch of EXAMPLE 3, and resin obtained from Preparative Method 4 was combined with digoxin and incorporated into a patch of EXAMPLE 4. The patches of EXAMPLES 2–4 were tested according to the In Vivo Test of Sustained Release described below.

In Vivo Test of Sustained Release

A patch of the invention was pressed in place on the buccal mucosa of a female beagle dog. Blood samples were drawn periodically after the placement of the patch and the blood level of the drug was determined by a standard assay for digoxin.

Results are shown in TABLE I, wherein the absence of an entry indicates a blood level of drug below the detection limit of the assay.

TABLE I

| | Blood Levels of Digoxin (ng/mL) | | |
| | | Example | |
| Time (hours) | 2 | 3 | 4 |
| --- | --- | --- | --- |
| 0.5 | 0.08 | 0.10 | — |
| 1 | 0.37 | — | 0.58 |
| 2 | 0.54 | 2.19 | 0.08 |
| 3 | 0.57 | 1.49 | 0.02 |
| 4 | 0.83 | 2.33 | 0.04 |
| 5 | 0.94 | 3.23 | 0.11 |
| 6 | 0.82 | 5.64 | 0.02 |
| 8 | 1.18 | 5.34 | 0.04 |
| 12 | 2.56 | 4.91 | 0.29 |
| 24 | 3.64 | 3.50 | 0.85 |

The patches adhered for the 24 hour period during which blood samples were drawn. TABLE I shows that the bioavailability of the digoxin is substantial for a period of at least 24 h and that digoxin is delivered in a sustained fashion from these bioadhesive compositions of the invention.

EXAMPLES 5–7

Solutions containing VISTANEX™ L-100 polyisobutylene (0.25 g, as 1.25 g of a solution containing 20% VISTANEX™ L-100 polyisobutylene by weight in a 1:1 mixture by volume of hexane and toluene) and VISTANEX™ LM-MH polyisobutylene (1.0 g, as 2.00 g of a solution containing 50% VISTANEX™ LM-MH polyisobutylene by weight in a 1:1 mixture by volume of hexane and toluene) were prepared. The solutions were-combined, and theophylline (0.75 g) was added with stirring. Resins obtained from Preparative Methods 2, 3, and 4 (3.0 g) were independently added with stirring. The resulting mixtures were made into patches of EXAMPLES 5, 6, and 7, respectively, according to the method set forth in EXAMPLE 1.

EXAMPLES 8–14

Using the general method of EXAMPLES 2–4, individual patches comprising the compositions listed in TABLE II below, wherein the elastomer is a 1:4 mixture of VISTANEX™ L-100 polyisobutylene and VISTANEX™ LM-MH polyisobutylene, were prepared. TABLE II lists the resin used and the amount thereof, the type and amount of drug used, and the amount of elastomer used. All amounts are based upon the total weight of the bioadhesive composition.

TABLE II

| Example | Resin (%) | % Elastomer | Drug (%) |
|---|---|---|---|
| 8 | CARBOPOL ™934P (45%) | 40% | Morphine (15%) |
| 9 | CARBOPOL ™951 (45%) | 40% | Morphine (15%) |
| 10 | CARBOPOL ™910 (50%) | 35% | Morphine (15%) |
| 11 | CARBOPOL ™910 (45%) | 40% | Morphine (15%) |
| 12 | CARBOPOL ™910 (50%) | 35% | Morphine Sulfate (15%) |
| 13 | CARBOPOL ™910 (45%) | 40% | Morphine Sulfate (15%) |

TABLE II-continued

| Example | Resin (%) | % Elastomer | Drug (%) |
|---|---|---|---|
| 14 | CARBOPOL ™910 (50%) | 35% | Morphine HCl (15%) |

Patches of EXAMPLES 10, 12, and 14 were tested according to the In Vivo Test of Sustained Release (set forth in EXAMPLES 2–4 above) with a standard assay for morphine being employed. The results are shown in TABLE III.

TABLE III

Blood Levels of Morphine (ng/mL)

| Time (hours) | Example 10 | Example 12 | Example 14 |
|---|---|---|---|
| 1 | 11 | 8 | 17 |
| 2 | 18 | 15 | 38 |
| 3 | 18 | 19 | 76 |
| 4 | 16 | 26 | 26 |
| 6 | 25 | 16 | 59 |
| 8 | 13 | 12 | 33 |
| 10 | 25 | 10 | 19 |
| 12 | 16 | 10 | 12 |
| 24 | 49 | 16 | — |

The patches adhered throughout the 24 hour period during which blood samples were drawn. TABLE III shows that the bioavailability of morphine, morphine HCl, and morphine sulfate is substantial for a period of at least 24 h, and that these drugs are released from these compositions of the invention in a sustained fashion.

EXAMPLES 15–25

Using the general method of EXAMPLE 1, 5.0 g samples of the bioadhesive compositions set forth in TABLE IV below were prepared. All amounts are based upon the total weight of the bioadhesive composition. Individual patches were prepared according to the general method of EXAMPLE 1 and remained adhered to human buccal mucosa for a study period indicated in TABLE IV. The study period was terminated by removing the patch by hand. No entry indicates that the patch was adhered but was removed after a short time. Patches of EXAMPLES 20 and 24 were tested for in vivo adhesion in humans according to Step (2) of the Test Method set forth above. The results are shown in TABLE V below.

TABLE IV

| COMPONENT | EXAMPLE (wt %) | | | | | | | | | | |
|---|---|---|---|---|---|---|---|---|---|---|---|
| | 15 | 16 | 17 | 18 | 19 | 20 | 21 | 22 | 23 | 24 | 25 |
| CARBOPOL ™910 | 50 | 60 | 40 | — | — | — | — | — | — | — | — |
| CARBOPOL ™934P | — | — | — | — | — | 60 | 50 | 40 | — | — | — |
| CARBOPOL ™940 | — | — | — | 60 | — | — | — | — | — | — | — |
| CARBOPOL ™941 | — | — | — | — | 60 | — | — | — | — | — | — |
| CARBOPOL ™951 | — | — | — | — | — | — | — | — | 40 | 60 | — |
| CARBOPOL ™1342 | — | — | — | — | — | — | — | — | — | — | 60 |
| VISTANEX ™LMMH | 40 | 32 | 48 | 32 | 32 | 32 | 40 | 48 | 48 | 32 | 32 |
| VISTANEX ™L100 | 10 | 8 | 12 | 8 | 8 | 8 | 10 | 12 | 12 | 8 | 8 |
| Study Period | 24 h | 24 h | — | 2 h | 2 h | 24 h | 24 h | — | 20 h | 24 h | 4 h |

TABLE V

Duration of Adhesion (hours)

| Subject | Patch of Example 20 | Patch of Example 24 |
|---|---|---|
| A | 26 | 15 |
| B | 30 | 24 |
| C | 23 | 23 |
| D | 20 | 24 |
| E | 13 | 22 |
| F | 9 | 14 |
| Average (± σ) | 20.2 (± 7.3) | 20.3 (± 4.2) |

The data in TABLE V show that these patches of the invention adhere to human oral mucosa for an extended period of time.

EXAMPLES 26–29

CARBOPOL™ 910 resin (100 g) was placed in a Hobart mixer (Model N-50, Hobart Corp., Troy, Ohio) and mixed at a setting of 1 while isopropyl alcohol (100 ml) was added dropwise over a period of about 5 minutes. The resulting material was dried overnight in a tray oven at 32° C. and milled in a small mill (Fitzpatrick Model J, Fitzpatrick Co., Elmhurst, Ill.) to afford CARBOPOL™ 910 resin with an average particle size of about 30 μm to 50 μm.

Using the general method of EXAMPLE 1, and the CARBOPOL™ 910 resin as processed above, 5.0 g samples of the bioadhesive compositions set forth in TABLE VI were prepared. All amounts are based upon the total weight of the bioadhesive composition. Individual patches were prepared according to the general method of EXAMPLE 1 and remained adhered to human buccal mucosa for a study period of about 20 hours. The study period was terminated by removing the patch by hand.

TABLE VI

| Example No. | % CARBOPOL ™ 910 | % VISTANEX ™ LM-MH | % VISTANEX ™ L-100 |
|---|---|---|---|
| 26 | 50 | 40 | 10 |
| 27 | 60 | 32 | 8 |
| 28 | 70 | 24 | 6 |
| 29 | 75 | 20 | 5 |

EXAMPLES 30–32

Using the general method of EXAMPLE 1, 5.0 g samples of the compositions set forth in TABLE VII below were prepared. All amounts are based upon the total weight of the bioadhesive composition. The polyacrylic acid samples were purchased from Polysciences, Inc., Warrington, Pa. Individual patches were prepared according to the general method of EXAMPLE 1 and remained adhered to human buccal mucosa for a study period of about 4 hours. The study period was terminated by removing the patch by hand.

TABLE VII

| Example No. | % Polyacrylic Acid (MW) | % VISTANEX ™ LMMH | % VISTANEX ™ L100 |
|---|---|---|---|
| 30 | 50 (450,000) | 40 | 10 |
| 31 | 50 (1,000,000) | 40 | 10 |
| 32 | 50 (4,000,000) | 40 | 10 |

EXAMPLE 33

A solution (5.0 g) containing 70% by weight toluene, 10% by weight mineral oil, and 20% by weight of Kraton™ D 1107 rubber was prepared. Polycarbophil (Biomimetics, Inc., Lexington, Mass.) was added over a period of about 5 minutes with stirring. Patches were made from the resulting mixture as described in EXAMPLE 1. The patches remained strongly adhered to human buccal mucosa for a study period of several minutes. The study period was terminated by removing the patch by hand.

EXAMPLES 34 AND 35

A copolymer of 96% by weight isooctylacrylate and 4% by weight acrylamide (prepared according to the method of Example 2 of U.S. Pat. No. 4,751,087 (wick), the entire disclosure of which is incorporated herein by reference) was dissolved in a 90:10 (V/V) solution of ethyl acetate in methanol in an amount sufficient to prepare a 30% by weight solution of the copolymer. To an aliquot of the solution was added with stirring polycarbophil (Biomimetics, Inc., Lexington, Mass.) in an amount sufficient to prepare the compositions set forth in TABLE VIII below.

TABLE VIII

| Example | % Elastomer | % polycarbophil |
|---|---|---|
| 34 | 25 | 75 |
| 35 | 20 | 80 |

The compositions of TABLE VIII were made into patches according to the general method of EXAMPLE 1. The patches remained adhered strongly to human buccal mucosa for a study period of about 2 hours. The study period was terminated by removing the patch by hand.

EXAMPLES 36–43

Compositions were prepared by milling the components listed in TABLE IX at room temperature in a two-roll mill (Reliable Mill Model 3216, Rubber and Plaster Machine Company, North Bergen, N.J.) according to the general method set forth below.

The lower molecular weight component of the elastomer was added to the mill and milled until it was distributed on the rollers. The higher molecular weight component of the elastomer was then added as small pieces and milling was continued until a homogeneous mixture obtained. The plasticizer (if any) was then added and the mixture was milled until homogeneous.

The particulate polymeric resin was mixed with the drug (if any) to form a uniform mixture. The resin was then added slowly to the elastomeric component in the mill and this mixture was milled until a uniform composition obtained. It was necessary to periodically remove the material from the rollers, form it into a ball and re-mill to ensure a uniform composition. The composition was removed from the mill by scraping the rollers.

About 15 to 25g of the composition was pressed at about 70,000 KPa between two 17 cm×17 cm pieces of silicone-coated release liner in a platen press heated to about 50° C. to afford a laminate comprising a sheet of composition about 2 mm thick. Individual patches were cut from the resulting laminate with a die.

Compositions were prepared as described above using the materials set forth in TABLE IX below. Individual patches were found to adhere to human oral mucosa.

TABLE IX

| | Example Number | | | | | | | |
|---|---|---|---|---|---|---|---|---|
| Component | 36 | 37 | 38 | 39 | 40 | 41 | 42 | 43 |
| polycarbophil* | 30 g | 30 g | 30 g | | | 30 g | 30 g | 30 g |
| CARBOPOL ™934-P | | | | 90 g | 35 g | | | |
| LIR-50** | 12 g | | | | | | | |
| LIR-410** | | 12 g | | | | | | |
| LIR-506** | | | 12 g | | | | | |
| VISTANEX ™L-100 | 8 g | 8 g | 8 g | | | 9.8 g | 4 g | 4 g | 4 g |
| VISTANEX ™L-80 | | | | 30 g | | | | |
| VISTANEX ™LM-MH | | | | | 4.5 g | 16 g | 16 g | 16 g |
| mineral oil | | | | | 3 g | | | |
| corn oil*** | | | | | | | 3 g | |
| silicone oil**** | | | | | | | | 3 g |

TABLE IX-continued

| | Example Number | | | | | | | |
|---|---|---|---|---|---|---|---|---|
| Component | 36 | 37 | 38 | 39 | 40 | 41 | 42 | 43 |

*from Biomimetics, Inc., Lexington, MA
**from Arakawa Chemical, Chicago, IL
***MAZOLA™ Corn Oil
****Dow Corning 200 fluid, 200 cps

EXAMPLES 44–47

Compositions were prepared according to the general method set forth in EXAMPLES 36–43 above using the components shown in TABLE X below. TEGADERM™ 1625 surgical dressing was adhered as a backing to one side of the compositions.

TABLE X

| | Example | | | |
|---|---|---|---|---|
| Component | 44 | 45 | 46 | 47 |
| Vistanex ™LM-MH | 16 g | 16 g | 8 g | 9.6 g |
| Vistanex ™L-100 | 4 g | 4 g | 2 g | 2.4 g |
| Polycarbophil* | 30 g | 30 g | 15 g | 16 g |
| Theophylline | 10 g | | | |
| Digoxin | | | 0.2 g | |
| Estradiol | | 0.53 g | | |
| Nitroglycerin | | | | 2.0 g |

*Biomimetics, Inc., Lexington, MA

Individual patches of the composition of EXAMPLE 44 were prepared and placed on the gum of a female beagle dog and blood levels of the drug were measured using a standard assay. The results are shown below.

| Time (hr) | Theophylline level (μg/mL) |
|---|---|
| 1 | 0.5 |
| 3 | 1.0 |
| 5 | 1.4 |
| 7 | 1.4 |
| 10 | 1.2 |
| 14 | 1.2 |
| 21 | 1.4 |
| 24 | 1.2 |

The patch was removed after 24 hours

Individual patches of the composition of EXAMPLE 45 were prepared and two patches were placed on the gum of a female beagle dog and blood levels of both estradiol and estrone were measured using standard assays. The results are shown below.

| Time (hr) | Estradiol level (pg/mL) | Estrone level (pg/mL) |
|---|---|---|
| Predose | <5 | 12 |
| 0.25 | 13 | 46 |
| 0.5 | 17 | 87 |
| 1.0 | 39 | 170 |
| 1.5 | 58 | 230 |
| 2.0 | 43 | 220 |
| 3.0 | 330 | 1090 |
| 4 | 230 | 780 |
| 6 | 190 | 410 |

-continued

| Time (hr) | Estradiol level (pg/mL) | Estrone level (pg/mL) |
|---|---|---|
| 8 | 870 | 2040 |
| 24 | 110 | 420 |
| 25 | 39 | 130 |
| 30 | 13 | 40 |

The patch was removed at 24 hours.

Individual patches of the composition of EXAMPLE 46 were prepared and placed on the gum or the cheek of a female beagle dog as indicated below and blood levels of the drug were measured using a standard assay. The results are shown below, where nd designates that no determination of blood level of drug was made.

| | Digoxin level (ng/mL) | |
|---|---|---|
| Time (hr) | Gum | Cheek |
| 0.5 | <0.1 | <0.1 |
| 1 | <0.1 | 0.5 |
| 2 | 0.13 | 0.52 |
| 3 | 0.13 | 1.3 |
| 4 | 0.45 | 1.1 |
| 5 | 0.38 | 1.77 |
| 6 | 0.38 | nd |
| 7 | 0.47 | nd |

The patch was removed at 8 hours.

Individual patches of the composition of EXAMPLE 47 were prepared and placed on the inner surface of the upper lip of a female beagle dog and blood levels of the drug were measured using a standard assay. The results are shown below.

| Time (hr) | Nitroglycerin level (ng/mL) |
|---|---|
| Predose | 0.0 |
| 1 | 2.5 |
| 2 | 4.3 |
| 3 | 4.5 |
| 4 | 13.0 |
| 5 | 12.8 |
| 6 | 0.60 |

The patch was removed at 5 hours.

In all cases, therapeutic levels of the respective drug were observed for a sustained period of time.

EXAMPLES 48–53

Compositions were prepared by milling at room temperature in a two-roll mill (Model Number 53060 Farrell-Birmingham Ansonia Conn.) with rollers of 15 cm diameter and 30 cm length according to the general method set forth below. The elastomeric component or, in the case of a two-component elastomeric component, the higher molecular weight component, was added to the mill in portions and milled until uniform (about 15 minutes) and rolled into a sheet. The sheet was placed in the mill, and the resin or, in the case of a two-component elastomeric component, the resin and the lower molecular weight component together, were added slowly and milled until a uniform composition obtained. The drug was then added and milling was continued until the drug was uniformly distributed in the composition (about 15 minutes). The composition was then rolled out of the mill in the form of a sheet by adjusting the space between the rollers such that a sheet of the desired thickness (e.g., 1-2 mm) was produced. Individual patches were cut from the resulting sheet with a 1 cm² circular die.

Compositions were prepared as described above using the components set forth in TABLE XI below.

Using conventional methods, the compositions of EXAMPLES 48, 49, and 50 were found to have uniform drug content throughout the compositions. A patch of the composition of EXAMPLE 51 remained adhered to the buccal mucosa of a female beagle dog for a study period of 24 hours. Patches of the compositions of EXAMPLES 52 and 53 remained adhered to human buccal mucosa for a study period of about 8 hours and about 15 hours, respectively. The study periods were terminated by removing the patches by hand.

An approximately square sheet with an area of about 25 cm² of a composition was prepared by the general milling method of EXAMPLES 48–53 using 75% by weight of CARBOPOL™ 934P resin and 25% by weight VISTANEX™ L-80 polyisobutylene.

As a backing layer, an approximately square sheet with an area of about 25 cm² of VISTANEX™ L-100 polyisobutylene was prepared according to the general method of EXAMPLE 1 (absent the resin and the backing), by solvent casting the solution of elastomer at a wet thickness of about 0.5 mm.

The three sheets were stacked with the milled patch in the middle. The stacked compositions were pressed between two sheets of release liner in a heated platen press at 38° C. and 35,000 KPa. A 1 cm² circular patch was cut from the resulting composition. The patch remained adhered to human gingival mucosa for a study period of about 14 hours. The study period was terminated by removing the patch by hand. The layers of the patch showed no sign of de-laminating, and the polyisobutylene backing layer prevented adhesion of the patch to the mucosal surface opposite the gum.

EXAMPLES 56–58

Patches were prepared according to the general method of EXAMPLES 48–53 above, using the components set forth in TABLE XIII below.

TABLE XI

| | Component (wt. %) | | | | | |
|---|---|---|---|---|---|---|
| Example | Vistanex ™L-100 | Vistanex ™L-80 | Vistanex ™LMMH | Carbopol ™934P | Theophylline | Morphine Sulfate |
| 48 | 17 | — | 8.5 | 59.5 | | 15 |
| 49 | | 21.25 | | 63.75 | | 15 |
| 50 | | 22.5 | | 67.5 | 10 | |
| 51 | 20 | | | 60 | | 20 |
| 52 | | 25 | | 75 | | |
| 53 | 20 | | 10 | 70 | | |

EXAMPLE 54

A composition was prepared according to the general method of EXAMPLES 36–43 using 60% by weight polycarbophil, 32% by weight VISTANEX™ LMMH polyisobutylene, and 8% by weight VISTANEX™ L-100 polyisobutylene. A circular patch of 1.2 cm diameter was prepared and placed in the vaginal cavity of a sheep. After a period of about 20 hours, the patch was still adhering well and was slightly swollen. After a period of about 44 hours, the patch was still adhering well, but some disintegration was observed. After a period of about 70 hours, the patch was still adhering but it was soft and swollen. The patch was removed by gentle scraping with a spatula.

EXAMPLE 55

A multi-layer gradient composition was prepared as follows:

An approximately square sheet with an area of about 25 cm² of the solvent-cast composition of EXAMPLE 15 was prepared.

TABLE XII

| | Component (wt. %) | | | |
|---|---|---|---|---|
| Example | NATSYN™ 2210 | NATSYN™ 2205 | CARBOPOL™ 934P | Theo-phylline |
| 56 | 20 | — | 50 | 30 |
| 57 | 20 | — | 60 | 20 |
| 56 | — | 20 | 60 | 20 |

The above-described patches were independently adhered to a glass slide using double-stick tape and tested for in vitro release of theophylline by immersing the patches in 700 mL of pH 7 buffer solution in a USP Type II dissolution apparatus. Periodically, a 5 mL aliquot of the buffer was removed and analyzed by ultraviolet spectrophotometry (270 nm) for theophylline. Results are as shown in TABLE XIII below.

TABLE XIII

| Time (hours) | % theophylline released Example | | |
|---|---|---|---|
| | 56 | 57 | 58 |
| 0.25 | 9.66 | 8.64 | 11.08 |
| 0.50 | 14.66 | 13.18 | 17.16 |
| 1.0 | 22.60 | 20.76 | 26.76 |
| 1.5 | 29.45 | 27.35 | 35.68 |
| 2 | 35.34 | 33.03 | 44.32 |
| 3 | 46.03 | 43.56 | 60.27 |
| 4 | 55.48 | 53.33 | 73.24 |
| 5 | 63.84 | 61.97 | 82.70 |
| 6 | 71.23 | 69.62 | 90.00 |
| 7 | 77.40 | 76.29 | 94.46 |
| 8 | 83.56 | 81.82 | 97.30 |
| 16 | 100 | 100 | 100 |

The data in TABLE XIII show that these compositions of the invention release theophylline in a sustained fashion in vitro.

EXAMPLE 59

A patch was prepared using 20 weight percent NATSYN™ 2210 polyisoprene (Goodyear, molecular weight about 760,000), 50 weight percent CARBOPOL™ 934P resin, and 30 weight percent morphine sulfate, with the sheet of composition being pressed at about 70° C. and about 70,000 KPa for about 20 seconds prior to cutting into patches. Morphine sulfate release in vitro was determined as described above in connection with EXAMPLES 56–58, with the buffer aliquot being analyzed for morphine by the USP method. Results are shown in TABLE XIV below.

TABLE XIV

| Time (minutes) | % morphine released |
|---|---|
| 20 | 1.34 |
| 30 | 2.79 |
| 60 | 6.43 |
| 90 | 8.25 |
| 120 | 11.75 |
| 180 | 15.62 |
| 240 | 19.60 |
| 360 | 27.21 |
| 480 | 33.67 |
| 600 | 40.33 |
| 720 | 44.58 |

The data in TABLE XIV show that the composition of EXAMPLE 59 releases morphine sulfate in a sustained fashion in vitro.

EXAMPLE 60

A patch was prepared according to the general method of EXAMPLES 48–53 using 30 weight percent NATSYN™ 2205 polyisoprene (molecular weight about 955,000) and 70 weight percent CARBOPOL™ 934P resin. The patch was adhered to the gingival mucosa of a subject and remained adhered for a study period of about 8 hours, after which time the study period was terminated and the patch was removed from the mucosa.

EXAMPLE 61

A patch was prepared according to the general method of EXAMPLES 48–53 above using 30 weight percent TAKTENE™ 1202 polybutadiene (Polysar, molecular weight about 375,000) and 70 weight percent CARBOPOL™ 934P resin. The patch was placed on the gingival mucosa of a subject and remained adhered for a study period of about 7 hours after which time the study period was terminated and the patch was removed from the mucosa.

EXAMPLES 62–63

Two different embodiments of patches were prepared according to the general method of EXAMPLES 48–53 above, using, respectively, 5 weight percent TAKTENE™ 1202 polybutadiene (molecular weight about 335,000), 25 weight percent NATSYN™ 2210 polyisoprene (molecular weight about 760,000), and 70 weight percent CARBOPOL™ 934P resin; and 25 weight percent TAKTENE™ 1220 polybutadiene, 5 weight percent NATSYN™ 2210 polyisoprene, and 70 weight percent CARBOPOL™ 934P resin, with the respective sheets being pressed as described in Example 59 above prior to cutting into patches.

The patches were found to adhere to human oral mucosa.

EXAMPLE 64

According to the general method of EXAMPLE 1 above, a composition of the invention was prepared using 45 weight percent CARBOPOL™ 934P resin, 18 weight percent VISTANEX™ L-100 polyisobutylene, 27 weight percent VISTANEX™ LMMH polyisobutylene, and 10 weight percent melatonin. Patches made from this composition were placed on the oral mucosa of dogs and found to provide therapeutically effective blood levels of melatonin.

We claim:

1. A bioadhesive composition that comprises;
   1) a particulate polymeric resin polymerized from monomers selected from the group consisting essentially of acrylic acid, itaconic acid, citraconic acid, and methacrylic acid that contains at least about 55% by weight of carboxylic acid groups based on the total weight of the polymeric resin and comprises less than about 20% by weight, based on the total weight of all monomers in the polymer, of esthetically unsaturated comonomers; and
   2) from about 20 parts to about 250 parts by weight of a hydrophobic elastomeric synthetic polymer component, based on 100 parts by weight of the resin elastomeric synthetic polymer component selected from the group consisting essentially of a block synthetic-butadiene-styrene copolymer, a block styrene-isoprene-styrene copolymer, a polyisobutylene, a polybutadiene, an isoprene rubber, a carboxy-functional polyisoprene, a hydroxy-functional polyisoprene, an acrylate elastomer, or a mixture of two or more of the foregoing, wherein the resin is dispersed substantially throughout the elastomeric component, and which composition adheres to a mucosal surface.

2. A composition according to claim 1, wherein the polymeric resin consists essentially of acrylic acid monomer units.

3. A composition according to claim 1, wherein up to about 30% of the carboxylic acid moieties of the resin are neutralized by a base.

4. A composition according to claim 1, wherein the elastomeric component comprises a polyisoprene with a molecular weight of about 500,000 to about 1,200,000 a polybutadiene with a molecular weight of about 100,000 to about 500,000, or a mixture thereof.

5. A composition according to claim 1, wherein the elastomeric component is a mixture comprising about 5% to about 50% by weight of a polyisobutylene with a viscosity average molecular weight between about 500,000 and about 2.5 million, and about 50% to about 95% by weight of a polyisobutylene with a viscosity average molecular weight between about 40,000 and about 100,000.

6. A composition according to claim 1, wherein the resin has an average particle size between about 1 μm and about 80 μm.

7. A composition according to claim 1, wherein the resin has an average particle size of between about 2 μm and about 10 μm.

8. A composition according to claim 1, comprising about 20 to about 150 parts by weight of the elastomeric component based on 100 parts by weight of the resin.

9. A composition according to claim 1, comprising about 25 to about 75 parts by weight of the elastomeric component based on 100 parts by weight of the resin.

10. A composition according to claim 1, which contains less than about 4% water by weight based on the total weight of the resin.

11. A composition according to claim 1, which contains less than about 2% water by weight based on the total weight of the resin.

12. A composition according to claim 1, wherein said composition includes an effective amount of a drug to provide a desired therapeutic result and the drug is a narcotic analgesic.

13. A composition according to claim 1, wherein said composition includes an effective amount of a drug to provide a desired therapeutic result and the drug is morphine or a pharmaceutically acceptable salt thereof.

14. A composition according to claim 1, wherein said composition includes an effective amount of a drug to provide a desired therapeutic result and the drug is selected from the group consisting of digoxin, heparin, hydromorphone, buprenorphine, theophylline, melatonin, and pharmaceutically acceptable salts thereof.

15. A composition according to claim 1, wherein the resin is distributed substantially uniformly throughout the elastomeric component.

16. A composition according to claim 1, wherein the resin is distributed throughout the elastomeric component in a suitable gradient.

17. A composition according to claim 1, wherein said composition includes an effective amount of a drug to provide a desired therapeutic result and the drug is distributed substantially uniformly throughout the elastomeric component.

18. A composition according to claim 1, wherein said composition includes an effective amount of a drug to provide a desired therapeutic result and the drug is distributed throughout the elastomeric component in a suitable gradient.

19. A bioadhesive composition adhered to a mucosal surface, said composition comprising:

1) a particulate polymeric resin polymerized from monomers selected from the group consisting essentially of acrylic acid, itaconic acid, citraconic acid, and methacrylic acid with an average particle size of less than or equal to about 100 μm that contains at least about 55% by weight of carboxylic acid groups based on the total weight of the polymeric resin and comprises less than about 20% by weight, based on the total weight of all monomers in the polymer, of ethylenically unsaturated comonomers; and 2) from about 20 parts to about 250 parts by weight of a hydrophobic elastomeric synthetic polymer component, based on 100 parts by weight of the resin, said elastomeric synthetic polymer component selected from the group consisting essentially of a block styrene-butadiene-styrene copolymer, a block styrene-isoprene-styrene copolymer, a polyisobutylene, a polybutadiene, an isoprene rubber, a carboxy-functional polyisoprene, a hydroxy-functional polyisoprene, an acrylate elastomer, or a mixture of two or more of the foregoing, wherein the resin is dispersed substantially throughout the elastomeric component, and which composition exhibits a duration of adhesion to mucosa of at least about 6 hours when tested according to the Test Method.

20. A transmucosal patch comprising:

1) a flexible film backing; and 2) a bioadhesive composition on one surface of the flexible film, the bioadhesive composition comprising i) a particulate polymeric resin polymerized from monomers selected from the group consisting essentially of acrylic acid, itaconic acid, citraconic acid, and methacrylic acid with an average particle size of less than or equal to about 100 μm that contains at least about 55% by weight of carboxylic acid groups based on the total weight of the polymeric resin and comprises less than about 20% by weight, based on the total weight of all monomers in the polymer, of ethylenically unsaturated comonomers; and ii) from about 20 parts to about 250 parts by weight of a hydrophobic elastomeric synthetic polymer component, based on 100 parts by weight of the resin, said elastomeric synthetic polymer component selected from the group consisting essentially of a block styrene-butadiene-styrene copolymer, a block styrene-isoprene-styrene copolymer, a polyisobutylene, a polybutadiene, an isoprene rubber, a carboxy-functional polyisoprene, a hydroxy-functional polyisoprene, an acrylate elastomer, or a mixture of two or more of the foregoing, wherein the resin is dispersed substantially throughout the elastomeric component, and adheres to a mucosal surface, which patch is further characterized in that it exhibits a duration of adhesion to mucosa of at least about 6 hours when tested according to step 2 of the Test Method.

21. A method of achieving and/or maintaining a therapeutically effective blood level of a drug in a mammal, which method comprises the steps of:

a) adhering to a mucosal surface of a mammal a composition including a drug and a bioadhesive, wherein the bioadhesive includes a particulate polymeric resin polymerized from monomers selected from the group consisting essentially of acrylic acid, itaconic acid, citraconic acid, and methacrylic acid having at least about 55% by weight of carboxylic acid groups based on the weight of the resin, and comprises less than about 20% by weight, based on the total weight of all monomers in the polymer, of ethylenically unsaturated comonomers dispersed substantially throughout from about 20 parts to about 250 parts by weight of a hydrophobic elastomeric synthetic polymer component, based on 100 parts by weight of the particulate polymeric resin, said elastomeric synthetic polymer component selected from the group consisting essentially of a block styrene-butadiene-styrene copolymer, a block styrene-isoprene-styrene copolymer, a polyisobutylene, a polybutadiene, an isoprene rubber, a carboxy-functional polyisoprene, a hydroxy-functional polyisoprene, an acrylate elastomer, or a mixture of two or more of the foregoing; and b) allowing the composition to remain adhered for a time sufficient to release drug such that a therapeutically effective blood level of drug is achieved and/or maintained.

22. A method of achieving and/or maintaining a therapeutically effective blood level of a drug in a mammal, which method comprises the steps of:

a) adhering to a mucosal surface of a mammal a patch including the drug and a bioadhesive on at least one surface of the patch, wherein the bioadhesive includes a particulate polymeric resin polymerized from monomers selected from the group consisting essentially of acrylic acid, itaconic acid, citraconic acid, and methacrylic acid that contains least about 55% by weight of carboxylic acid groups based on the weight of the resin and comprises less than about 20% by weight, based on the total weight of all monomers in the polymer, of ethylenically unsaturated comonomers, dispersed substantially throughout from about 20 to about 250 pats by weight of a hydrophobic elastomeric synthetic polymer component, based on 100 parts of the particulate polymeric resin, said elastomeric synthetic polymer component selected from the group consisting essentially of a block styrene-butadiene-styrene copolymer, a block styrene-isoprene-styrene copolymer, a polyisobutylene, a polybutadiene, an isoprene rubber, a carboxy-functional polyisoprene, a hydroxy-functional polyisoprene, an acrylate elastomer, or a mixture of two or more of the foregoing; and b) allowing the patch to remain adhered for a time sufficient to release drug such that a therapeutically effective blood level of drug is achieved and/or maintained.

23. A method of delivering a drug to a mucosal surface of a mammal or to the vicinity of a mucosal surface of a mammal to provide a therapeutic effect on or in the vicinity of the mucosal surface, which method comprises the steps of:

a) adhering a composition to the mucosal surface, said composition including a drug and a bioadhesive, wherein the bioadhesive includes a particulate polymeric resin polymerized from monomers selected from the group consisting essentially of acrylic acid, itaconic acid, citraconic acid, and methacrylic acid that contains at least about 55% by weight of carboxylic acid groups based on the weight of the resin and comprises less than about 20% by weight, based on the total weight of all monomers in the polymer, of ethylenically unsaturated comonomers, dispersed substantially throughout from about 20 to about 250 parts by weight of a hydrophobic elastomeric synthetic polymer component, based on 100 parts of the particulate polymeric resin, said elastomeric synthetic polymer component, selected from the group consisting essentially of a block styrene-butadiene-styrene copolymer, a block styrene-isoprene-styrene copolymer, a polyisobutylene, a polybutadiene, an isoprene rubber, a carboxy-functional polyisoprene, a hydroxy-functional polyisoprene, an acrylate elastomer, or a mixture of two or more of the foregoing;

b) allowing the composition to remain adhered for a time sufficient to release the drug to the mucosal surface or to the vicinity of the mucosal surface to provide the desired therapeutic effect.

24. A composition according to claim 1, wherein the hydrophobic elastomeric component comprises a polyisobutylene and a polyisoprene.

25. The bioadhesive composition of claim 1, further comprising an amount of a drug effective to provide a desired therapeutic result.

26. The bioadhesive composition of claim 25, wherein the drug is dispersed substantially throughout the bioadhesive.

27. The bioadhesive composition of claim 1, wherein said composition is adhered to an oral mucosal surface.

28. The bioadhesive composition of claim 1, wherein said composition adheres to a mucosal surface for a duration of at least about 6 hours when tested according to step 2 of the Test Method.

29. The bioadhesive composition of claim 1, wherein said composition adheres to a mucosal surface for a duration of at least about 8 hours when tested according to step 2 of the Test Method.

30. The bioadhesive composition of claim 1, wherein said composition adheres to a mucosal surface for a duration of at least about 12 hours when tested according to step 2 of the Test Method.

31. The bioadhesive composition of claim 1, wherein the particulate polymeric resin has an average particle size of less than about 100 μm.

32. The bioadhesive composition of claim 1, wherein said composition contains less than about 10% water by weight based on the total weight of the resin.

33. The method of claim 1, wherein the bioadhesive exhibits substantially no instantaneous adhesion to dry skin.

34. The bioadhesive composition of claim 19, further comprising an amount of a drug effective to provide a desired therapeutic result.

35. The bioadhesive composition of claim 34, wherein the drug is dispersed substantially throughout the bioadhesive.

36. The transmucosal patch of claim 20, further comprising an amount of a drug effective to provide a desired therapeutic result.

37. The transmucosal patch of claim 36, wherein the drug is dispersed substantially throughout the bioadhesive.

38. The patch of claim 20, wherein said patch exhibits a duration of at least about 8 hours when tested according to step 2 of the Test Method.

39. The transmucosal patch of claim 20, wherein said patch exhibits a duration of adhesion of at least about 12 hours when tested according to step 2 of the Test Method.

40. The transmucosal patch of claim 20, wherein the particulate polymeric resin is a polyacrylic resin.

41. The transmucosal patch of claim 20, wherein the particulate polymeric resin has an average particle size of less than about 100 μm.

42. The transmucosal patch of claim 20, wherein the bioadhesive contains less than about 10% water by weight based on the total weight of the resin.

43. The method of claim 20, wherein the bioadhesive exhibits substantially no instantaneous adhesion to dry skin.

44. The transmucosal patch of claim 43, wherein the hydrophobic elastomeric component includes polyisobutylene and polyisoprene.

45. The method of claim 22, wherein the patch is adhered to an oral mucosal surface.

46. The method of claim 45, wherein the patch remains adhered to a human oral mucosal surface for a duration of at least about 6 hours.

47. The method of claim 45, wherein the patch remains adhered to a human oral mucosal surface for a duration of at least about 8 hours.

48. The method of claim 45, wherein the patch remains adhered to a human oral mucosal surface for a duration of at least about 12 hours.

49. The method of claim 22, wherein the particulate polymeric resin has an average particle size of less than about 100 µm.

50. The method of claim 22, wherein the bioadhesive has a water content of less than about 10% by weight of the resin.

51. The method of claim 22, wherein the particulate polymeric resin is a polyacrylic resin.

52. The method of claim 22, wherein the hydrophobic elastomeric component includes a polyisobutylene and a polyisoprene.

* * * * *

UNITED STATES PATENT AND TRADEMARK OFFICE
CERTIFICATE OF CORRECTION

PATENT NO.: 5,750,136

DATED: May 12, 1998

INVENTOR(S): Matthew T. Scholz, Robert A. Scherrer, Nelda M. Marecki, Yen-Lane Chen, and Joan K. Barkhaus It is certified that error appears in the above-identified patent and that said Letters Patent is hereby corrected as shown below:

Col. 24, line 43, "esthetically" should be --ethylenically--.

Col. 24, line 47-48, "resin elastomeric" should read --resin, said elastomeric--.

Col 24, line 50, "synthetic-butadiene-styrene" should read --styrene-butadiene-styrene--.

Signed and Sealed this

Ninth Day of February, 1999

Attest:

Attesting Officer

Acting Commissioner of Patents and Trademarks